(12) United States Patent
Loyan et al.

(10) Patent No.: US 11,478,031 B2
(45) Date of Patent: Oct. 25, 2022

(54) CELLULITE DIMINISHING FABRIC

(71) Applicant: Sanko Tekstil Isletmeleri San. Ve Tic. A.S., Inegol—Bursa (TR)

(72) Inventors: Kenan Loyan, Inegol—Bursa (TR); Leyla Zengi, Inegol—Bursa (TR); Fatma Korkmaz, Inegol—Bursa (TR); Günes Banazili, Inegol—Bursa (TR); Merve Nagihan Akçay, Inegol—Bursa (TR); Turan Eren Gül, Inegol—Bursa (TR)

(73) Assignee: Sanko Tekstil Isletmeleri San. Ve Tic. A.S., Inegol—Bursa (TR)

( * ) Notice: Subject to any disclaimer, the term of this patent is extended or adjusted under 35 U.S.C. 154(b) by 402 days.

(21) Appl. No.: 15/938,556

(22) Filed: Mar. 28, 2018

(65) Prior Publication Data
US 2018/0279705 A1   Oct. 4, 2018

(30) Foreign Application Priority Data
Mar. 31, 2017   (EP) .................................... 17164239

(51) Int. Cl.
*A41D 31/00*   (2019.01)
*D03D 1/00*   (2006.01)
(Continued)

(52) U.S. Cl.
CPC ............. *A41D 31/14* (2019.02); *A41D 31/04* (2019.02); *A41D 31/18* (2019.02); *D03D 1/00* (2013.01); *D03D 15/56* (2021.01); *D06C 7/00* (2013.01); *D06M 23/04* (2013.01); *D06M 23/16* (2013.01); *D06N 3/0006* (2013.01); *D06N 3/0029* (2013.01); *D06N 3/0043* (2013.01); *D06N 3/0077* (2013.01); *D06N 3/0086* (2013.01); *D06N 3/042* (2013.01); *D06N 3/128* (2013.01); *D06N 3/14* (2013.01); *D06N 3/183* (2013.01); *A41B 2400/82* (2013.01); *A41D 2400/322* (2013.01); *A41D 2400/82* (2013.01);
(Continued)

(58) Field of Classification Search
CPC ........................................................ D06Q 1/00
USPC ........................................................ 428/195.1
See application file for complete search history.

(56) References Cited

U.S. PATENT DOCUMENTS

2006/0100312 A1*  5/2006  Hall ..................... D06P 1/44
                                                           523/201
2007/0033696 A1   2/2007  Sellier
(Continued)

FOREIGN PATENT DOCUMENTS

CN   105495738   4/2016
EP   2444547   4/2012

OTHER PUBLICATIONS

"Fabric Testing," Hu, Woodhead Publishing (Year: 2008).*
(Continued)

*Primary Examiner* — Ian A Rummel
(74) *Attorney, Agent, or Firm* — Silvia Salvadori

(57) ABSTRACT

Disclosed is a fabric having a first side and a second side, that is provided at least on part of the first side with a pattern of protrusions, wherein the protrusions comprise an expanded heat-expanding material, namely a heat-expanding material that has been expanded by heating. A polymeric layer is provided to the woven fabric to coat at least part of the protrusions. Also disclosed is a process for the production of the fabric and a garment comprising the fabric.

18 Claims, 7 Drawing Sheets

(51) Int. Cl.
| | |
|---|---|
| *D06C 7/00* | (2006.01) |
| *D06N 3/00* | (2006.01) |
| *D06N 3/14* | (2006.01) |
| *D06N 3/04* | (2006.01) |
| *D06N 3/12* | (2006.01) |
| *D06N 3/18* | (2006.01) |
| *A61F 13/08* | (2006.01) |
| *A41D 13/00* | (2006.01) |
| *A41D 31/14* | (2019.01) |
| *D06M 23/04* | (2006.01) |
| *D06M 23/16* | (2006.01) |
| *A41D 31/18* | (2019.01) |
| *A41D 31/04* | (2019.01) |
| *D03D 15/56* | (2021.01) |

(52) U.S. Cl.
CPC .......... *A61F 13/08* (2013.01); *D06N 2209/06* (2013.01); *D06N 2211/10* (2013.01); *D06N 2211/106* (2013.01); *D06N 2211/24* (2013.01); *D10B 2401/04* (2013.01); *D10B 2501/00* (2013.01); *D10B 2509/00* (2013.01)

(56) References Cited

U.S. PATENT DOCUMENTS

| | | |
|---|---|---|
| 2015/0366281 A1 | 12/2015 | Miller |
| 2015/0366735 A1 | 12/2015 | Barker |
| 2016/0100636 A1 | 4/2016 | Grandin De L'eprevier |
| 2017/0087924 A1* | 3/2017 | Aihara .................. B44C 3/025 |

OTHER PUBLICATIONS

European Search Report dated Jul. 20, 2017 for European priority application on 17164239.0.
International Search report and written opinion dated May 11, 2018 for corresponding PCT/EP2018/058217.
Office action issued by the CN Patent Office dated Aug. 20, 2021 for corresponding CN application No. 201810282055.4.

* cited by examiner

CELLULITE DIMINISHING FABRIC

RELATED APPLICATION

This application is related to and claims priority to European application No. 17164239.0 filed 31 Mar. 2017, the contents of which are hereby incorporated by reference as if set forth in their entirety.

TECHNICAL FIELD

The present invention relates to fabrics, in particular to fabrics intended to provide beneficial effects to the wearer, garments formed of the fabric and methods for forming the fabric.

BACKGROUND

Cellulite affects a great number of women and consists of deposits of subcutaneous fat within fibrous connective tissue (e.g. in the thighs, hips, and buttocks) that give a puckered and dimpled appearance to the skin surface. Garments serving to combat cellulite are known in the art.

For example, several known garments are designed to provide a beneficial effect against cellulite by making the wearer sweat.

However, this kind of garment usually does not provide satisfactory results. Garments providing a "massage effect" to the wearer are also known.

EP2444547A2 discloses a process for manufacturing a non-woven fabrics with abrasive properties of varying level for the purpose of cleaning, from gentle cosmetic cleansing to household cleaning and beyond. The process comprises a step of screen printing on wet fabric a desired shape using a paste that expands under heating by virtue of a puffing agent contained therein.

US2015/366735A1 discloses an item of clothing that is adapted to be worn against the skin, and includes at least one panel adapted to provide targeted compression of at least 20% of the total length of a specific surface vein in the body, or adapted to provide targeted compression of at least 20% of a specific plexus of veins, a specific lymphatic plexus, drainage plexus or a collection of lymphatic vessels. US2015/366735A1 discloses that the item of clothing of is useful in a method of reducing recovery time in a human or other mammal, after a period of activity and in a method of enhancing performance, in particular sports performance, in a human or other mammal. US2015/366735A1 discloses that the panel may be continuous or discontinuous, and may be built up by depositing a suitable plastics or other material, e.g. by ink-jet printing, or by the application of pre-made transfers. US2015/366281A1 discloses a fabric having resilient prominences on at least one surface, for improved thermal protection, drag reduction and quick drying. US2015/366281A1 discloses that resilient prominences are bulges that extend outward from a fabric surface and trap some volume of air or other material therein. A resilient prominence is resilient in shape, whereby the resilient prominence may be compressed and then popped back into substantially the original shape.

US2007/0033696 discloses elastic garments, intended to help the wearer to fight cellulite, comprising projection structures, protuberances or a bumpy composition, on the inner side of the garment corresponding to the desired area to be contacted by the projection structures. According to US2007/0033696, the aim of the projection structures, is to change the curvature of the knitted garment locally when worn, thus increasing the compression exerted by the garment in the aforesaid desired area.

Similarly, US2016/0100636 discloses a garment comprising at least one sleeve, having at least one region, the inner surface of which is equipped with a network of picots, wherein the picots have a trigonal base and are distributed in the network so as to form alveoli between adjacent picots, the sleeve being designed such that the picots can exert pressure on the skin great enough to form a skin protrusion in at least one alveolus in order to micro-massage the protrusion during relative movements taking place between the network and the body part, thus providing a "pinching" effect to the skin.

However, the known garments designed to provide a beneficial effect against cellulite are usually specifically intended for use during physical exercise and do not provide the aesthetical appearance required by a garment in order to be suitable for daily use.

Additionally, the protrusions may be damaged, even in a short time of use, for example because of the stretching and contracting of the fabric, as well as because of the friction with the body of the wearer. As a result, the protrusions lose their structure and their efficacy in contrasting the cellulite. Moreover, the friction of the protrusions with the skin of the wearer may cause discomfort in wearing the garment (especially when the protrusions are damaged or have lose their structure) and may also cause irritation of the skin of the wearer.

Furthermore, the processes for the production of known garments designed to provide a beneficial effect against cellulite are generally difficult to manage and expensive. In particular, complex processes have to be carried out in order to provide a fabric or a garment with protrusions having specific features, such as a specific height and/or a specific dimension.

SUMMARY

An aim of the present invention is thus to provide a fabric that provides beneficial effect to the wearer that can be produced in an easy, fast and inexpensive manner.

Another aim of the invention is to provide a fabric that provides beneficial effect to the wearer, and that is comfortable to wear, even for prolonged time, and that can be used in garments for daily life.

Still another aim of the present invention is to provide a fabric that resists to prolonged use substantially without damages.

A further aim of the present invention is to provide a process for producing a fabric, as above mentioned, and garments comprising said fabric.

Therefore, an object of the present invention is a fabric, having a first side and a second side, the fabric having a plurality of protrusions at least on part of the first side as a pattern of protrusions, wherein the protrusions comprise an expanded heat-expanding material.

In other words, the present invention refers to a fabric, such as a woven fabric, having a first side and a second side, which comprises a plurality of protrusions; the protrusions provided at least on part of the first side as a pattern of protrusions, and comprise a heat-expanding material that has been expanded by heating.

In other words, the protrusions of the fabric of the invention comprise a material has been expanded by heating, i.e. by a heat-treatment, to provide the fabric with tridimensional structures, i.e. "protuberances" or "protrusions". According to an aspect of the invention, the first side of the fabric is the side of the fabric which contacts the body of the wearer when a clothing article, i.e. a garment, comprising the fabric of the invention is worn. The protrusions of the fabric of the invention provide a massage to the body of the wearer, thus providing a beneficial effect to the wearer, in particular in diminishing or alleviating the cellulite.

According to various embodiments, protrusions are provided to the surface of the first side of the fabric, and may be provided on substantially the entire surface of the first side of the fabric.

According to an advantageous aspect of the invention, since the protrusions comprise an "expanded" heat-expanding material, it is possible to generate the protrusions directly on the fabric.

For example, a heat-expanding material (or a mixture comprising it) may be applied to the fabric, e.g. by printing, and, subsequently, the printed fabric may be heated to induce the expansion (i.e. the swelling) of the heat-expanding material applied on the fabric.

In this way, when the heat-expanding material (or a mixture comprising it) is applied to the fabric as a plurality of elements (namely a plurality of substantially bi-dimensional elements), a plurality of protrusions (i.e. substantially tridimensional structures) is formed directly on the fabric, by heat-treating the fabric provided with such elements.

As used herein, the term "substantially bi-dimensional" refers to elements having a negligible thickness with respect to the other two physical dimensions, i.e., elements that are substantially "flat". This term encompasses the specific case wherein the elements are "bi-dimensional".

As used herein, the term "heat-expanding material" refer to a material which increases its volume when exposed to heat, and that is suitable to be applied, e.g. printed, to a fabric to form tridimensional structures.

As used herein, the term "expanded heat-expanding material" refers to a heat-expanding material that has been subjected to heating (i.e. heat-treatment), so that its volume is increased, to provide tridimensional structures (e.g., protrusions).

According to an aspect of the invention, once the heat-expanding material has been "expanded" a first time, it cannot be further expanded by a second heat-treatment.

For example, suitable heat-expanding materials are polymeric heat-expanding materials.

Heat-expanding materials suitable to be applied, e.g. by printing, to fabrics and garments are known in the art.

The heat-expanding material may be an expanding ink. Expanding inks are known in the art (e.g. expanding ink puff). For example, a suitable expanding ink may be included into an acrylic polymer based printing paste, for example, into a silicone acrylic polymer based printing paste.

Another advantage of the present invention is that, by using a heat-expanding material (e.g. an expanding ink) protrusions with different dimension (e.g. different height) may be obtained, directly on the fabric, by adjusting the parameters of heating (i.e. of the heat-treatment).

In other words, for example, the same amount of the same heat-expanding material, may be used to provide different patterns of protrusions having different structural features, e.g. protrusions with different height.

It is thus possible to produce a great variety of different fabrics by simply adjusting the conditions and the parameters of the production process, such as, for example, the amount of heat-expanding material provided, the heating temperature and the duration of the heat-treatment, thus saving time, energy and costs.

A further advantage of the fabric of the present invention is that it induces an increase of the temperature at the level of the skin of a user wearing a garment which is made at least in part with the fabric of the invention, thus providing further beneficial effects in reducing and alleviating cellulite. In fact, without being bound to a specific scientific explanation, it has been observed that, in addition to a massage effect, the mechanical friction of the fabric of the invention on the skin of a user provides for an increase of the temperature of the skin of the user. For example, mechanical friction between the fabric of the invention and the skin of a user may occur with every-day activity movements and/or with physical exercise.

According to advantageous embodiments of the invention, at least part of the protrusions are coated with a polymeric layer.

Advantageously, it has been observed that by providing a polymeric layer to at least part of the protrusions of the fabric, i.e. providing a polymeric layer between the protrusions and the skin of the wearer, a fabric that provides beneficial effect to the wearer, and that is comfortable to wear, even for prolonged time, is obtained.

Without being bound to a specific explanation, it has been observed that, by coating at least part of the protrusions of the fabric with a polymeric layer, the skin of the user contacts a smooth and soft surface (in particular protrusions having a smooth and soft surface) which, at the same time, effectively provides a massage effect to the wearer's body and provides for a comfort feeling when the garment is used, even for prolonged time. Also, when a polymeric layer is provided to at least part of the protrusions on the fabric, a further increase in the temperature at the level of the skin of a user wearing a garment comprising the fabric is obtained, in particular when a mechanical friction of the fabric on the skin of the user occurs.

Additionally, the polymeric layer protects the protrusions from possible damages, thus further prolonging the life of the fabric and, therefore, the life of the garments comprising it.

According to embodiments, the polymeric layer is a polymeric film. In other words, the polymeric layer may have a thickness that is negligible in comparison with the height of the protrusions. In this case, the polymeric layer is such that it does not substantially affect the profile of the pattern of protrusions. In other words, the protrusions have substantially the same dimension and height both with or without being provided with the polymeric layer.

According to embodiments, the protrusions are substantially completely coated, or are completely coated, with the polymeric layer. In this case, the protrusions are protected from possible damages, in their entire structure. According to embodiments, at least the first side of the fabric of the invention is substantially completely coated, or completely coated, with the polymeric layer. Advantageously, when the fabric of the invention has the first side, i.e. the side of the fabric which is provided with the protrusions, substantially completely coated, or completely coated, with the polymeric layer, the production process is particularly fast and easy.

According to some embodiments, the protrusions are completely coated with the polymeric layer.

The polymeric layer may advantageously be a polyurethane, such as a breathable polymeric layer.

Advantageously, when the polymeric layer comprises a polyurethane, the polymeric layer may be particularly smooth and soft.

As above mentioned, a plurality of protrusions is provided at least on part of the first side of the fabric of the invention as a pattern of protrusions.

According to a various embodiments, the protrusion are positioned in parallel staggered rows.

According to various exemplary embodiments, after the heat-treatment, the protrusions in a row are spaced apart from one another by a distance which may range from ⅕ of the width of a protrusion to 5 times the width of a protrusion, it may range from ⅓ of the width of a protrusion to 3 times the width of a protrusion, or it may range from ½ of the width of a protrusion to 2 times the width of a protrusion.

According to various embodiments, before the heat-treatment, the "protrusions" (which are, before the heat-treatment, not yet "protrusions", but substantially bi-dimensional elements comprising a heat-expanding material) are spaced apart from one another by a distance which ranges from equal to the width of a "protrusion" (i.e. a substantially bi-dimensional element) to two times the width of a "protrusion" (i.e. a substantially bi-dimensional element). According to embodiments before the heat-treatment, the substantially bi-dimensional elements (which increase in volume to provide protrusions upon heating) have a width that is two times smaller (one half) the blank space (i.e. the distance) between two substantially bi-dimensional elements. According to various embodiments, this measurement represents measurements prior to the heat-treatment. After the heat-treatment, i.e. after the formation of protrusions, these sizes (i.e. the distance between two protrusions and the width of the protrusions) may advantageously be equal to each other.

According to various embodiments, the protrusions in a row are spaced apart from one another by a distance which is substantially equal to the width of a protrusion.

As used herein, the term "width" is used to indicate the dimension of the protrusion measured in the direction of the row to which the protrusion belongs.

With the term "length", is herein indicated the dimension of the protrusion measured in orthogonal direction with respect to the direction of the row to which the protrusion belongs. As used herein, the expression "the dimension of the protrusion" may indicate the dimension of each of the protrusions according to the embodiment in which the protrusions all have substantially the same dimensions, or it may refer to the average dimension of the protrusions.

Where not otherwise indicated, the term "distance" refers to the distance between two "protrusions". In other words, where not otherwise indicated, the term "distance" refers to the fabric after the "expansion" (i.e. the "swelling") of the heat expanding material.

Accordingly, when a heat-expanding material is applied, before the heat-treatment, i.e. before the expansion, the heat-expanding material is applied onto the fabric as a pattern of elements, namely substantially bi-dimensional elements, comprising the heat expanding material, that, after heating, provides for a pattern of protrusions (comprising the expanded heat-expanding material) that are spaced apart by a selected distance.

The distance between two protrusions after the heat-treatment (i.e., after the "expansion") is in general smaller than the distance between the substantially bi-dimensional elements before the expansion of the heat-expanding material, i.e., before the heat-treatment.

In other words, for example, a heat-expanding material (or a mixture comprising it) may be printed onto the fabric according to a pattern of substantially bi-dimensional elements, wherein the elements of the pattern are spaced apart from one another by a certain distance. Subsequently, the printed fabric may be heated to induce the expansion (i.e. the swelling) of the heat-expanding material thus providing a pattern of protrusions that are spaced apart from one another by a distance that is smaller than the distance between the printed heat-expanding material elements before the heating.

As above mentioned, the protrusions may be positioned in parallel staggered rows and the protrusions may be spaced apart by the same distance in all the rows.

According to embodiments, the protrusions are positioned in parallel staggered rows so that a row is staggered with respect to the preceding row by a distance that is substantially equal, or equal, to the width of a protrusion. According to embodiments, the distance between two non-staggered rows (i.e. two non-adjacent rows, i.e. two rows that are separated by a staggered row) is higher than the distance between two adjacent protrusions in the same row.

According to embodiments, two non-staggered rows (i.e. two non-adjacent rows, i.e. two rows that are separated by a staggered row) are separated by a distance which is substantially equal, or equal, to the length of a protrusion. For example, the distance between two non-adjacent rows (i.e. two rows that are not staggered) may range from 0.1 mm to 5 mm, or from 0.2 mm to 3 mm, or from 0.25 mm to 2 mm in various embodiments.

According to various embodiments, the rows of protrusions are staggered so that a protrusion in a row is placed substantially in the middle of the distance between two protrusions in the preceding row and the following row. Alternatively stated, the protrusions may be arranged in staggered rows such that a first protrusion in a first row is disposed substantially halfway between two adjacent protrusions in the rows adjacent to the first row.

Advantageously, when the rows of protrusions are staggered so that a protrusion in a row is placed substantially in correspondence of the middle of the distance between two protrusions in the preceding row and the following row, it has been observed that the fabrics provides for "separated" point of pressure on the skin of the wearer.

In other words, when the rows of protrusions are staggered so that a protrusion in a row is placed substantially in correspondence of the middle of the distance between two protrusions in the preceding row and the following row, the distance between adjacent protrusions is so that the contact with the skin of each protrusion does not substantially affect the contact with the skin of another protrusion, thus providing for a particularly effective massage effect of the fabric to the skin of the wearer.

According to embodiments, the protrusions are positioned so that each protrusion is surrounded by 6 adjacent protrusions positioned according to a substantially hexagonal shape arrangement, or according to a hexagonal shape arrangement such as a substantially regular hexagonal shape arrangement, or a regular hexagonal shape arrangement.

As used herein, the terms "substantially hexagonal" and "substantially regular hexagonal" refer to two possible arrangement of the pattern of protrusions, when each protrusion is surrounded by 6 adjacent protrusions. In particular, the term "substantially hexagonal" refers to a shape arrangement wherein six protrusions surrounding a determined protrusion are arranged to represent the 6 vertices of a polygon having 6 edges. The term "substantially regular hexagonal" refers to a shape arrangement wherein the 6 edges of the polygon have approximatively the same length. The terms "substantially hexagonal" and "substantially regular hexagonal" encompasses the specific arrangements "hexagonal" and "regular hexagonal".

According to embodiments, the protrusion are positioned according a repeating unit formed by two protrusions, where the lower protrusion is staggered with respect to the upper protrusion when the pattern is viewed from above. This repeating unit is reproduced several times on the fabric to provide a pattern of protrusions, as above mentioned.

According to an aspect of the invention, the protrusions have a base which contacts the fabric.

According to embodiments of the invention, the shape of the base of the protrusions substantially corresponds to the shape of the substantially bi-dimensional elements comprising a heat-expanding material provided onto the fabric before the expansion, i.e. before the heat-treatment.

In other words, for example, a heat-expanding material (or a mixture comprising it) may be printed onto a fabric according to a pattern of substantially bi-dimensional elements having a selected shape. Subsequently, the printed fabric may be heated to induce the expansion (i.e. the swelling) of the heat-expanding material (to obtain an expanded heat-expanding material) thus providing a pattern of protrusions that contact the fabric with a base having a shape that substantially corresponds to the shape of the elements of the printed pattern before the heating. For example, if the substantially bi-dimensional elements of the printed pattern have a substantially oval, or oval (e.g. substantially elliptical, or elliptical) shape, the corresponding protrusions will have a base having a substantially oval, or oval (e.g. substantially elliptical, or elliptical) shape.

As used herein, the term "substantially oval" refers to a closed curvilinear shape which resemble an oval. The term "substantially oval" encompasses the specific oval shape. The term "elliptical shape" refer to a particular example or "oval shape", wherein the oval is an ellipse. The term "substantially elliptical shape" encompasses the specific elliptical shape.

As used herein, the term "substantially a circle" refers to a closed curvilinear shape which resemble a circle. This term encompasses the specific shape of a circle.

According to embodiments, the base of a protrusion (i.e. after the heat-treatment) has increased dimension with respect to the substantially bi-dimensional element (i.e. before the heat treatment) from which the protrusion derives.

According to embodiments of the invention, the protrusions have the shape of the base which may be substantially an oval (e.g. an ellipse), a circle or a polygonal shape.

For example, when the shape of the base is substantially an ellipse, the dimension of the major axis may range from 0.1 mm to 5 mm, it may range from 0.2 mm to 3 mm, or it may range from 0.25 mm to 2 mm, in various embodiments.

Moreover, when the shape of the base is substantially an ellipse, the dimension of the minor axis may range from 0.1 mm to 5 mm, or from 0.2 mm to 3 mm, or from 0.25 mm to 2 mm in various embodiments.

The ratio minor axis: major axis may advantageously be in the range of from 0.1 to 0.5.

Of course, in the case of an ellipse (or a substantially elliptical shape), the major axis is always longer than the minor axis.

For example, when the shape of the base is substantially a circle, the dimension of the diameter may range from 0.1 mm to 5 mm or it may range from 0.2 mm to 3 mm or from 0.25 mm to 2 mm in various embodiments.

When the shape of the base of the protrusion is substantially an ellipse, with the term "width" of the protrusion is indicated the dimension substantially corresponding to the minor axis of the ellipse.

Conversely, when the shape of the base of the protrusion is substantially an ellipse, with the term "length" of the protrusion is indicated the dimension substantially corresponding to the major axis of the ellipse.

According to embodiments, when the shape of the base of the protrusion is substantially a circle, both the "width" and the "length" of the protrusion substantially correspond to the diameter of the circle.

According to embodiments, the height of the protrusions is less (i.e., lower) than the thickness of the fabric, i.e. the distance separating the first side of the fabric from the second side.

The height of the protrusion may advantageously range from $1/10$ to $1/2$ of the thickness of the fabric. The height of the protrusion may range from $2/10$ to $2/5$ of the thickness of the fabric, or from $1/4$ to $3/10$ of the thickness of the fabric in various embodiments.

According to embodiments, the protrusions have a height ranging from 0.01 mm to 1 mm, or from 0.05 to 0.5 mm, or from 0.08 mm from 0.3 mm in various embodiments.

The protrusions may have an average height of 0.2 mm.

Advantageously, when the protrusion have the above mentioned height, the fabric of the invention may provide a massage effect (and thus a cellulite-alleviating action) to the body of the wearer without creating discomfort in the wearer.

According to some embodiments, all the protrusions have substantially the same height, or the same height. According to some embodiments, all the protrusions have substantially the length and width.

As used herein, the term "substantially the same height" refer to protrusions wherein the difference between the height of different protrusions is negligible. The term "substantially the same height" encompasses the case wherein all the protrusions have the same height.

The dimensions of the protrusions and of the polymeric layer are measured on a fabric that is not under tension, i.e. is not stretched.

The stiffness of the fabric may range from 2.5 to 0.95N, or from 2 to 0.75N, or from 15 to 0.5N, measured according to ASTM D4032.

Advantageously, when the fabric of the invention has a stiffness ranging from 2.5 to 0.95, measured according to ASTM D4032, the fabric is particularly comfortable on the skin of the user, which can move without difficulties wearing a garment comprising the fabric of the invention.

According to embodiments, the distribution of the protrusions on the first side of the fabric may range from 20 protrusions/cm$^2$ to 5 protrusions/cm$^2$, or the distribution of the protrusions on the first side of the fabric may range from 16 protrusions/cm$^2$ to 8 protrusions/cm$^2$. In some embodiments, the distribution of the protrusions on the first side of the fabric is 10 protrusions/cm$^2$.

According to embodiments, the distribution of the protrusions on the first side of the fabric may be homogeneous or not-homogeneous; in other words, the protrusion may have the same distribution throughout the whole fabric (e.g. throughout the whole first side of the fabric) or may have different distributions in different regions of the fabric. For example, a region of the fabric may have a distribution of protrusions of 20 protrusions/cm$^2$, while another region of the fabric may have a distribution of protrusions of 10 protrusions/cm$^2$.

As above mentioned, in various embodiments, a polymeric layer is provided to at least part of the protrusions of the fabric.

The polymeric layer may comprise a polyurethane, and, may be a breathable polymeric layer.

Advantageously, when the polymeric layer comprises a polyurethane, the polymeric layer is particularly smooth and soft.

According to embodiments, the polymeric layer has a thickness ranging from 0.001 mm to 0.05 mm, or the thickness may range from 0.0015 mm to 0.03 mm or from 0.002 mm to 0.02 mm in various embodiments.

As above mentioned, according to a preferred embodiment, the polymeric layer has a thickness that is negligible in comparison with the height of the protrusions; for example, the polymeric layer may be a polymeric film.

According to various embodiments, the fabric of the invention is a woven fabric and may be an elastic woven fabric.

The elasticity of the woven fabric in warp direction may be at least 10%, at least 15%, at least 50%, at least 75% or it may be up to 100% (measured according to ASTM D3107—Stretch, after 3 home washes) in various embodiments. The elasticity of the fabric in weft direction may be at least 10%, at least 15%, at least 50%, at least 75%, or it may be 100% (ASTM D3107—stretch, after 3 home washes) in various embodiments.

According to various embodiments, the elasticity of the woven fabric in warp direction and/or in weft direction ranges from 10% to 100%, from 15% to 100%, from 15% to 75%, or from 15% to 50% (measured according to ASTM D3107—Stretch, after 3 home washes).

An elasticity of up to 100% (measured according to ASTM D3107—Stretch, after 3 home washes) in warp direction and/or in weft direction advantageously allows the woven fabric of the invention to be stretched repeatedly without damaging the protrusions and/or the polymeric layer.

Also advantageously, an elasticity of up to 100% (measured according to ASTM D3107—Stretch, after 3 home washes) in warp direction and/or in weft direction allows for the production of a garment configured to be worn against the skin, so that a compression is exerted on the skin of a user.

In the ASTM D3107, a sample may be stretched by means of a weight of 3.0 lb or 4.0 lb. It has been proven that there are no significant differences in the test results if either a 3.0 lb or 4.0 lb weight is used. In the present disclosure, stretch according to ASTM D3107 was measured by means of a 3.0 lb weight.

According to embodiments, the fabric may be a uni-stretch fabric or a bi-stretch fabric.

In other words, the fabric may be a fabric that can be stretched in warp direction or in weft direction, or both in warp and weft direction.

According to embodiments, the fabric may be a multi-axis-stretchable fabric, i.e. a fabric that can be stretched in all directions.

The fabric of the invention may be a denim fabric, advantageously an elastic denim fabric.

Advantageously, when the fabric of the invention is a denim fabric, the fabric is particularly suitable for the production of garment for daily use, i.e., for the production of garment which provide for a beneficial effect against cellulite and that can be worn in every-day life.

Another object of the invention is a process for the production of a fabric comprising the following steps:
a. Providing a fabric having a first side and a second side.
b. Providing a pattern of substantially bi-dimensional elements of a heat-expanding material at least on part of the first side of the fabric.
c. Heat-treating the fabric obtained in step b. to obtain a pattern of protrusions comprising an expanded form of the heat-expanding material.

According to an aspect of the invention, once the heat-expanding material has been "expanded" a first time, it cannot be further expanded by a second heat-treatment.

In some embodiments, the process further comprises a step d. of coating at least part of the protrusions with a polymeric layer.

In some embodiments, the process further comprises a step of substantially completely coating, or completely coating, the first side of the fabric with the polymeric layer.

As above mentioned, according to an aspect of the invention, the first side of the fabric is the side of the fabric which contacts the body of the wearer when a clothing article, i.e. a garment, comprising the fabric of the invention is worn.

According to an aspect of the invention, the heat-expanding material (or a mixture comprising it) is provided to the fabric as a pattern of substantially bi-dimensional elements, spaced apart from one another by a selected distance.

According to an aspect of the invention, the heat-expanding material is applied to the fabric, e.g. by printing, as a pattern of substantially bi-dimensional elements and subsequently the fabric is heat-treated to obtain the protrusions, i.e. a pattern of protrusions.

For example, the heat-expanding material may be provided to the fabric in liquid form or in the form of a paste. The heat-treating increases the volume of the heat-expanding material, so that protrusions are obtained on the fabric. The heating temperature and time may be adjusted according to the chemical composition the heat-expanding material to obtain protrusions having the desired characteristics (e.g. height, dimension).

For example, when the heat-expanding material is an expanding ink, the woven fabric may be heat-treated at a temperature ranging from 100° C. to 210° C., from 130° C. to 200° C., or from 150° C. to 190° C. in various embodiments, to provide the "expansion" of the expanding ink, i.e., to obtain protrusions.

In various embodiments, the heat-expanding material is provided to the fabric by printing, thus providing a plurality of substantially bi-dimensional printed elements, i.e. a pattern of printed elements that are subsequently heat-treated to provide a pattern of protrusions.

Another object of the present invention is a fabric as obtainable according to step b. of the process of the invention, i.e. a fabric provided with a heat-expanding material on at least on part of its first side, before the heat-treatment.

Advantageously, a fabric as obtainable according to step b. of the process of the invention may be stored and heat-treated when needed.

Moreover, a fabric as obtainable according to step b. of the process of the invention may be included into a garment. In this case, advantageously, a user may heat-treat the garment in order to obtain a garment comprising a pattern of protrusions that comprise an expanded heat-expanding material, according to his needs.

A further object of the invention is a garment comprising a fabric according to the invention, i.e. a fabric having a first side and a second side, that comprises a plurality of protrusions that are provided at least on part of the first side of the fabric as a pattern of protrusions, wherein the protrusions comprise an expanded heat-expanding material, namely, a heat-expanding material that has been expanded by heating.

According to an aspect of the invention, the first side of the fabric, which is at least in part provided with a pattern of protrusions according to above, is the side which contacts the body of the user when the garment is worn.

Advantageously, a garment comprising the fabric of the invention, which may be a woven fabric, provides a massage effect to the body of the wearer, thus fighting and diminishing cellulite, and results to be comfortable also after a long time of wearing.

Also, a garment comprising the fabric of the invention advantageously provides for an increase of the temperature at the level of the skin of a user wearing the garment. Thus, in addition to a massage effect, the mechanical friction of the fabric of the invention on the skin of a user provides for an increase of the temperature of the skin of the user which may be associated with increased localized blood flow which may alleviate cellulite.

This is particularly true when the fabric is provided with a polymeric layer which coats at least part of the protrusions. In fact, in this case, it has been observed that a further increase in the temperature at the level of the skin of a user is obtained, in particular when a mechanical friction of the garment on the skin of the user occurs.

According to embodiments, the garment of the invention may comprise different parts, that are provided with different patterns of protrusions, i.e. pattern wherein the protrusions have, for example, different shape and/or height and/or distribution.

Advantageously, a garment can be configured as a "patch-work" of different embodiments of the woven fabric of the invention, thus providing to different parts of the garment, different massage effect.

According to embodiments, the garment of the invention may be a pair of pants, leggings, shorts, or a shirt, a t-shirt or a long sleeve shirt.

For example, the garment of the invention may be configured to be worn against the skin, so that a compression is exerted on the skin of a user.

The invention will be further disclosed with reference to the following figures that refer to exemplary and non-limiting embodiments and features of the invention.

DETAILED DESCRIPTION

The present invention relates to a fabric, having a first side and a second side, and including a plurality of protrusions, the protrusions being provided at least on part of the first side as a pattern of protrusions, wherein the protrusions comprise an expanded heat-expanding material, i.e. a heat-expanding material that has been expanded by heating.

In other words, the protrusion are provided by heat-treating a heat-expanding material, so that the heat-expanding material swells (i.e., "expands", i.e. increases its volume) when is heated, to provide a tridimensional structure, namely a protrusion.

Figure 1:
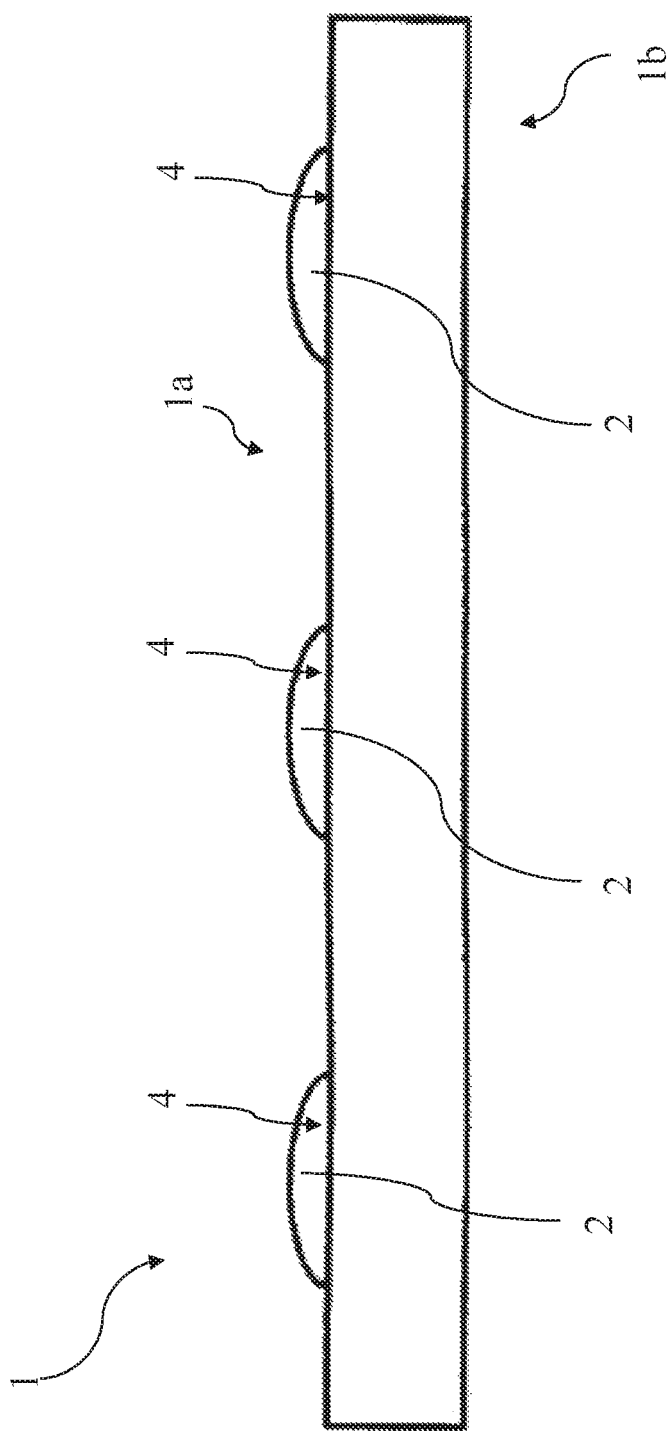
FIG. 1 is a schematic representations of the cross-sectional view of an embodiment of the fabric of the invention.

FIG. 1 is a schematic representations of the cross-sectional view of an embodiment of the fabric 1 of the invention.

FIG. 1 shows a fabric 1, having a first side 1a and a second side 1b.

On the first side 1a, a plurality of protrusions 2 are provided.

Each protrusion 2 has a base 4, which can be shaped, for example, as an oval (e.g., an ellipse), a circle or a polygon.

As above discussed, the pattern of protrusions 2 is provided to the fabric 1 by heat-treating a heat-expanding material, that was previously provided to the fabric 1, e.g. by printing.

In other words, a heat-expanding material, such as an expanding ink, may be printed onto the fabric 1 in order to provide a pattern of printed elements, that are substantially bi-dimensional. Subsequently, the printed fabric is heated, thus inducing the expansion of the heat-expanding material, which increases its volume, thus providing a pattern of tridimensional structures, i.e. a pattern of protrusions 2. Thus, as above mentioned, the protrusions 2 comprise an expanded heat-expanding material.

The shape of the base 4 of the protrusions 2, substantially corresponds to the shape of the printed elements which the protrusions 2 derive from; in other words, for example, if substantially bi-dimensional elements are printed on the fabric with an oval shape, the protrusions 2 deriving from such elements would have a base 4 having a substantially oval shape. According to various embodiments, the dimension of the base 4 of the protrusions 2, i.e., the area of the base 4, may be wider than the area of the printed elements which the protrusions 2 derive from. According to various embodiments, the dimension of the base 4 of the protrusions 2 may be wider than the area of the printed elements which the protrusions 2 derive from, and may have substantially the same shape, e.g., an oval shape. For example, a substantially bi-dimensional element having oval shape may be heat-treated to provide a protrusion 2 having a base 4, wherein the area of the base 4 is substantially an oval having an area which is wider than the area of the oval substantially bi-dimensional element which the protrusion 2 derives from.

According to an aspect of the invention, the protrusions 2 are provided at least on part of the first side 1a of the fabric 1, which is the side of the fabric 1 that contacts the body of a user, namely a person that wears a garment comprising the fabric 1, e.g. a pair of pants, when the garment is in use.

The protrusions 2 provide for a massage effect to the body of the wearer, thus providing beneficial effects in reducing cellulite.

In addition to a massage effect, the mechanical friction of the protrusions 2 on the skin of a user provides for an increase of the temperature of the skin of the user, thus providing further beneficial effects in reducing or diminishing cellulite. For example, mechanical friction between the protrusions 2 of the fabric 1 and the skin of a user may occur with every-day activity movements and/or with physical exercise.

The fabric 1 may be a woven fabric, and may advantageously be an elastic woven fabric.

For example the fabric 1 may be a denim fabric, such as an elastic denim fabric.

Figure 2:
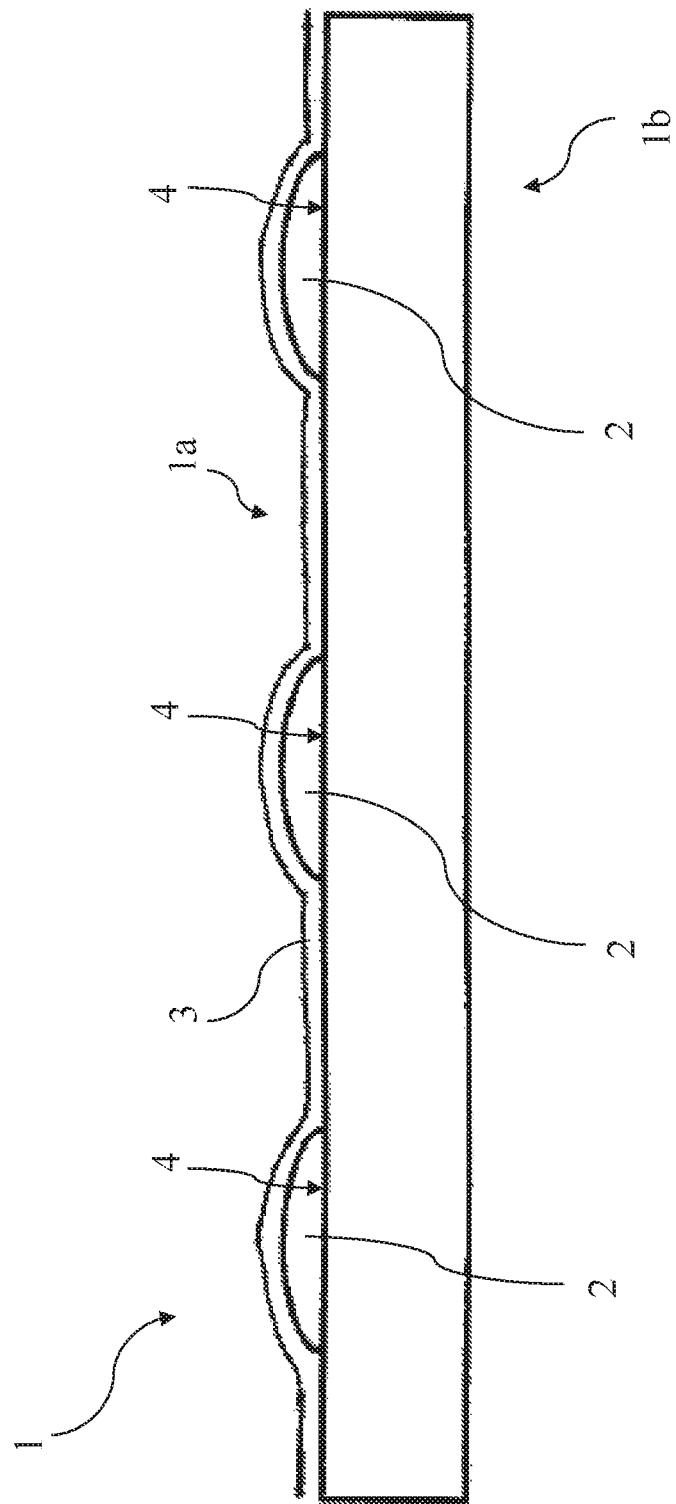
FIG. 2 and FIG. 3 are schematic representations of the cross-sectional view of two embodiments of the fabric of the invention provided with a polymeric layer.

FIG. 2 is a schematic representation of the cross-sectional view of an embodiment of the fabric of the invention when it is provided with a polymeric layer.

FIG. 2 shows a fabric 1, having a first side 1*a*, wherein a plurality of protrusions 2 are provided, and a second side 1*b*.

Each protrusion 2 has a base 4 which contacts the first side 1*a* of the fabric 1.

In the embodiment of FIG. 2, a polymeric layer 3 is provided to the fabric 1 to completely cover (i.e. completely coat) the first side 1*a* and the protrusions 2.

As above, the fabric 1 may be an elastic woven fabric; the elasticity of the woven fabric 1 may be at least 10%, at least 15%, at least 50%, or it may be at least 75%, or it may be up to 100% (measured according to ASTM D3107—Stretch, after 3 home washes) both in warp direction and weft direction, in various embodiments.

According to various exemplary embodiments, when the fabric 1 is an elastic woven fabric, the elasticity of the woven fabric in warp direction and/or in weft direction ranges from 10% to 100%, from 15% to 100%, from 15% to 75%, or from 15% to 50% (measured according to ASTM D3107—Stretch, after 3 home washes).

In this case, the protrusions 2 and the polymeric layer 3 are advantageously not adversely affected by prolonged use, namely by repeated stretching (i.e. elongation).

According to embodiments, the fabric 1 may be a uni-stretch fabric or a bi-stretch fabric; in other words, the fabric 1 may be a fabric that can be stretched in warp direction or in weft direction, or both in warp and weft direction.

According to embodiments, the fabric 1 may be a multi-axis-stretchable fabric, i.e. a fabric that can be stretched in all directions.

Advantageously, the polymeric layer 3, that is provided, in the embodiment illustrated in FIG. 2, to substantially completely cover or completely cover (i.e. substantially completely coat or completely coat) the first side 1*a* and the protrusions 2, protects the protrusions 2 from possible damages and deterioration and, moreover, it provides the fabric 1 (namely, the first side 1*a* comprising the protrusions 2) with a smooth surface, so that a garment comprising the fabric 1 results to be both effective in providing a cellulite-contrasting action and comfortable, smooth and soft on the skin of the wearer when the garment is worn.

Additionally, the polymeric layer 3 provides for a particularly high increase in the temperature at the level of the skin of a user wearing a garment comprising the fabric 1, in particular when a mechanical friction of protrusions 2 of fabric 1 on the skin of the user occurs.

Advantageously, the polymeric layer 3 is such that it does not substantially affect the profile of the pattern of protrusions 2. In this case, the polymeric layer 3 does not affect the massage effect provided by the protrusions 2, which is substantially the same both when the polymeric layer 3 is present or absent. According to embodiments, the polymeric layer 3 may be a polymeric film. Advantageously, the polymeric layer 3 provides the protrusions 2 with a smooth and soft surface.

Figure 3:
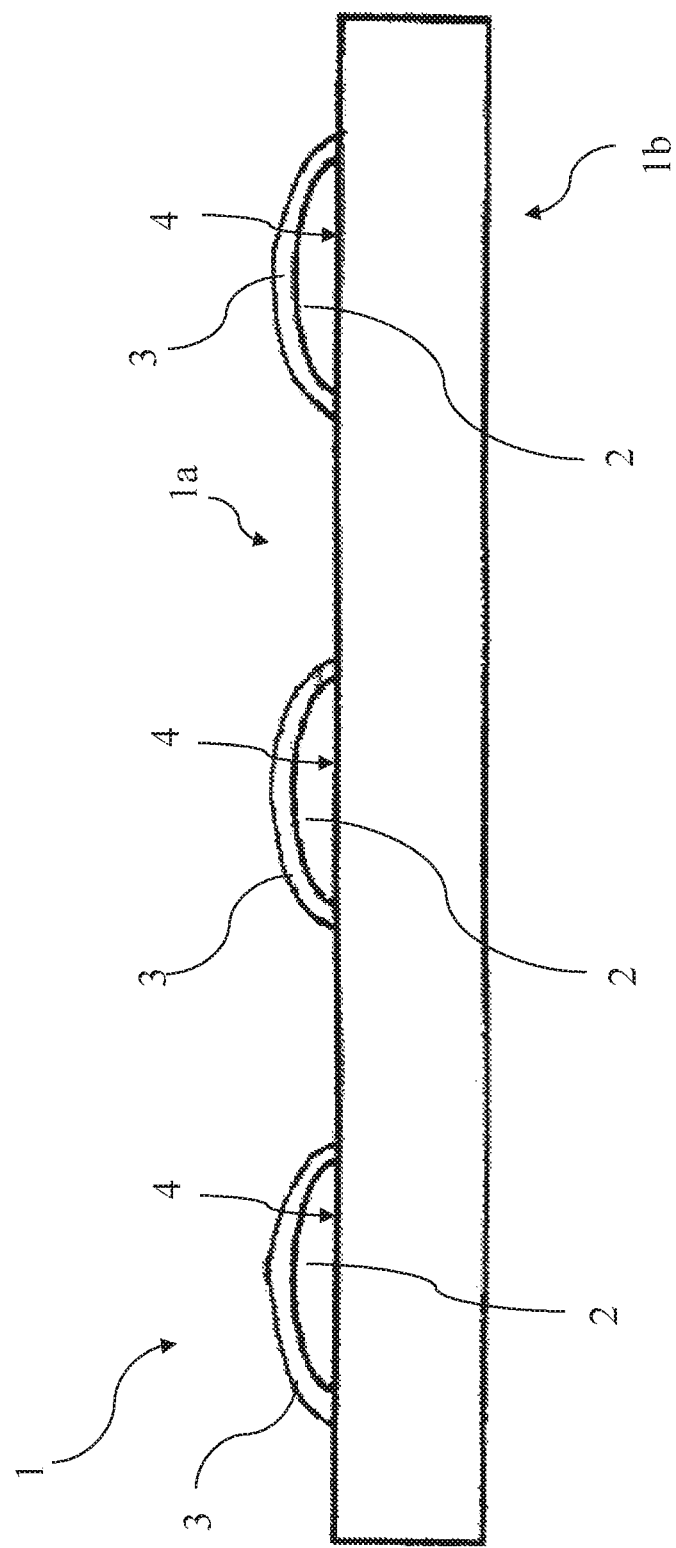

FIG. 3 shows an embodiment of the fabric 1 of the invention.

In the embodiment of FIG. 3 the polymeric layer 3 does not cover, namely does not coat, all the first side 1*a* of the fabric 1, but is provided as a coating for the protrusions 2.

Each protrusion 2 has a base 4.

Also in this case, the polymeric layer 3 provides the protrusions 2 with a smooth and soft surface. Additionally, the protrusions 2 are protected from possible damages, for example damages due to prolonged use.

Figure 4B:
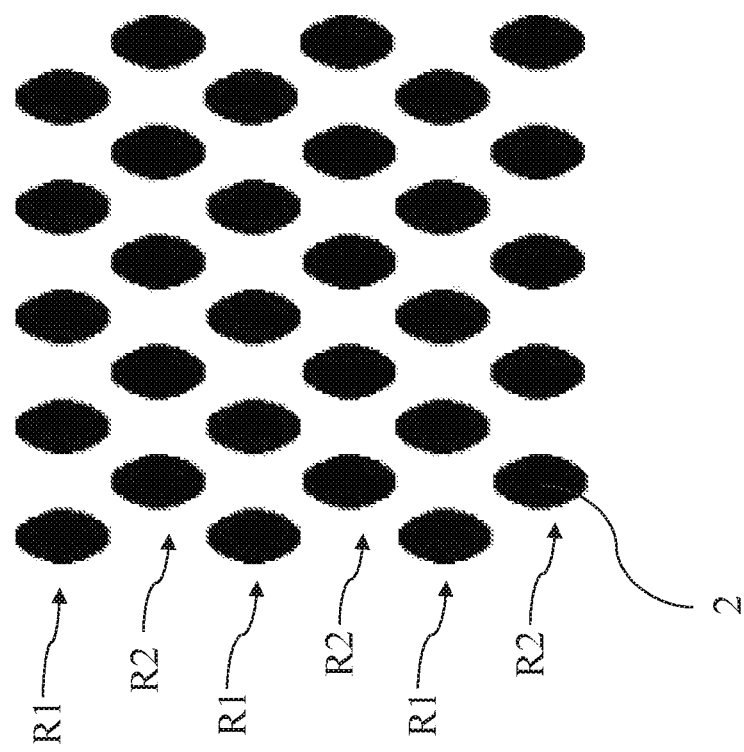
FIGS. 4A and 4B are illustrative examples of embodiments of the pattern of protrusions suitable to be used in the fabric of the invention.
Figure 4A:
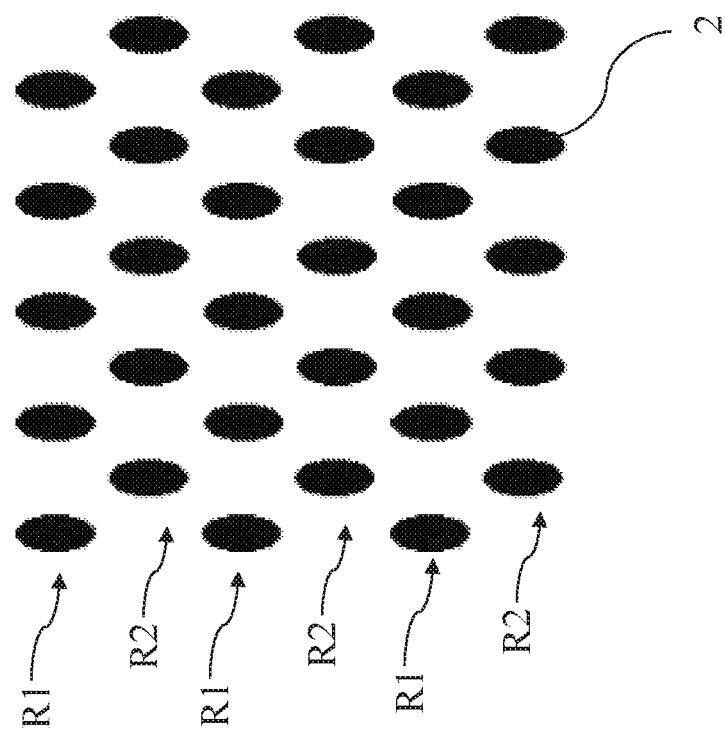

FIGS. 4A and 4B are illustrative examples of embodiments of the pattern of protrusions 2 suitable to be used in the fabric 1 of the invention.

FIGS. 4A and 4B show a top view of two patterns of protrusions 2 suitable to be provided to the fabric 1 (e.g. to the first side 1*a* of the fabric 1) of the invention. The shape of the protrusions 2 in the top views of FIGS. 4A and 4B corresponds to the shape of the base 4 of the protrusions 2 and, in this case, is substantially oval in both the embodiments of FIGS. 4A and 4B.

In FIG. 4A, as well as in FIG. 4B, all the protrusions 2 have the same dimension.

In FIGS. 4A and 4B the protrusions 2 are arranged in staggered rows R1, R2; namely, the protrusions 2 are arranged according to first rows R1 alternated with second rows R2, wherein second rows R2 are staggered with respect to first rows R1, and vice versa.

In FIGS. 4A and 4B the protrusions 2 are arranged in staggered rows R1, R2, so that each protrusion 2 in a first row R1 is placed substantially in the middle of the distance between two protrusions 2 in the preceding second row R2 and in the following second row R2.

In the same way, in FIGS. 4A and 4B the protrusions 2 are arranged in staggered rows R1, R2, so that each protrusion 2 in a second row R2 is placed substantially in the middle of the distance between two protrusions 2 in the preceding first row R1 and in the following first row R1.

According to the embodiments shown in FIGS. 4A and 4B, each protrusion 2 is surrounded by six adjacent protrusions 2 positioned to form a substantially hexagonal shape.

According to embodiments, protrusions 2 are provided substantially to the entire surface of the first side 1*a* of the fabric 1.

Figure 5:
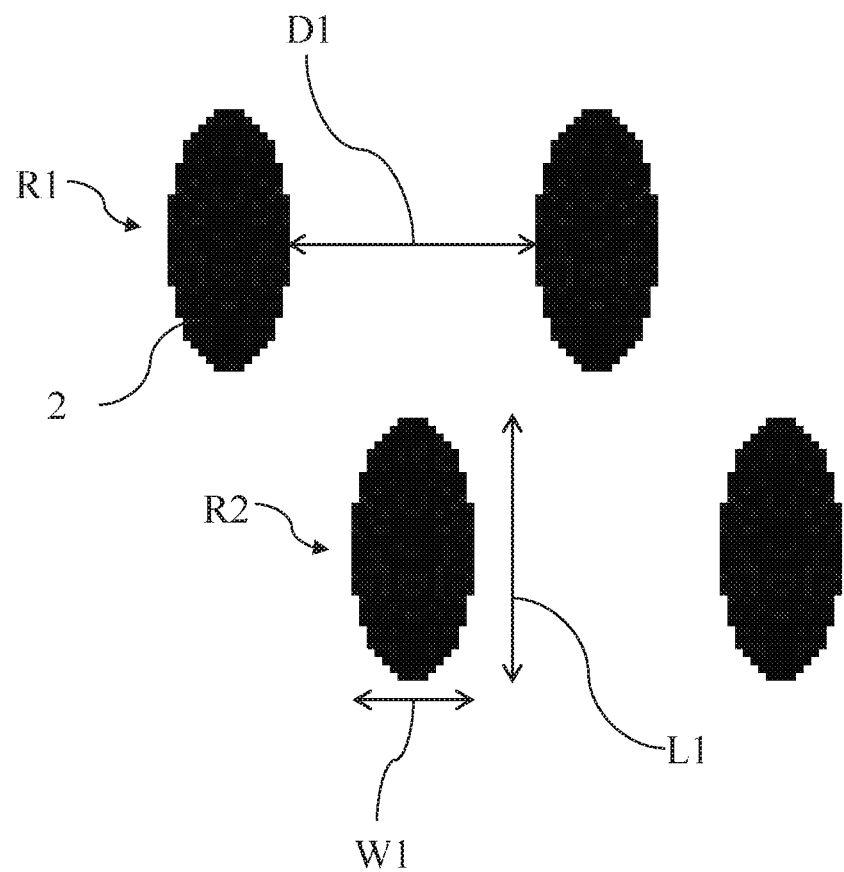
FIGS. 5 and 6 are schematic representations of embodiments of the protrusions of the fabric of the invention.
Figure 6:
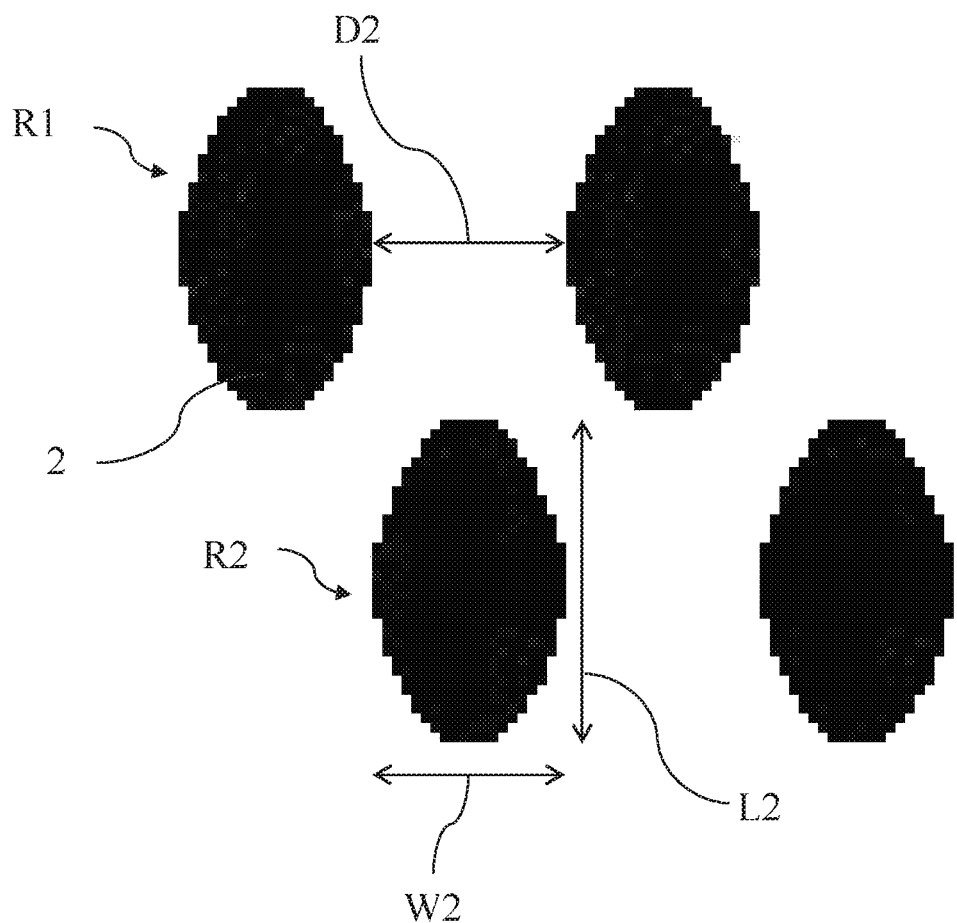

FIGS. 5 and 6 are schematic representations of embodiments of the protrusions 2 of the woven fabric 1 of the invention.

FIGS. 5 and 6 show a top view of two patterns of protrusions 2 suitable to be provided to the woven fabric 1 (e.g. to the first side 1*a* of the woven fabric 1) of the invention.

The shape of the top view of the protrusions 2 corresponds to the shape of the base 4 of the protrusions 2, and it is substantially elliptical in both the embodiments of FIGS. 5 and 6.

In FIG. 5, protrusions 2 have a first width W1 and first length L1; all the protrusions 2 have the same dimension, i.e. the same first width W1 and the same first length L1.

In FIG. 5, the first width W1 of the protrusion 2 substantially corresponds to the minor axis of the substantially elliptical shape of the base 4, and the first length L1 substantially corresponds to the major axis of the substantially elliptical shape of the base 4.

In FIGS. 5 and 6, the protrusions 2 are arranged in staggered rows R1, R2; schematically, in FIGS. 5 and 6 a first row R1, and a second row R2, which is staggered with respect of the first row R1, are shown.

FIG. 5 shows a pattern wherein two adjacent protrusions 2 in the first row R1 are spaced by a first distance D1; the same first distance D1 spaces two adjacent protrusions in the second row R2.

Moreover, FIG. 5 shows a pattern wherein two adjacent protrusions 2 in the same first row R1 and in the same second row R2 are spaced by a first distance D1 which is substantially 2 times the first width W1 of a protrusion 2. The protrusions 2 in the second row R2 are placed substantially in the middle of the first distance D1 between two protrusions 2 in the preceding first row R1.

In FIG. 6, protrusions 2 have a second width W2 and second length L2; all the protrusions 2 have the same dimension, i.e. the same second width W2 and the same second length L2.

Similarly to FIG. 5, also in the embodiment of FIG. 6 the second width W2 of the protrusion 2 substantially corresponds to the minor axis of the substantially elliptical shape of the base 4, and the second length L2 substantially corresponds to the major axis of the substantially elliptical shape of the base 4.

As in FIG. 5, also FIG. 6 shows a pattern wherein all the protrusions 2 have the same dimension, i.e. the same second width W2 and the same second length L2.

FIG. 6 shows a pattern wherein two adjacent protrusions 2 in the same first row R1 and in the same second row R2 are spaced by a second distance D2 which is substantially equal to the second width W2 of a protrusion 2.

For example, the protrusions 2 may have a width (first width W1; second width W2 in FIGS. 5 and 6 respectively) ranging from 0.1 mm to 5 mm, ranging from 0.2 mm to 3 mm, or ranging from 0.25 mm to 2 mm in various embodiments.

According to embodiments, two adjacent protrusions 2 in the same first row R1 and/or in the same second row R2 may be spaced by a distance (first distance D1; second distance D2 in FIGS. 5 and 6 respectively) which ranges from 0.1 mm to 5 mm, from 0.2 mm to 3 mm, or from 0.25 mm to 2 mm in various embodiments.

According to embodiments, the distance between two first rows R1 and/or between two second rows R2 (i.e. the distance between two first rows R1 that are separated by a staggered second row R2; and/or the distance between two second rows R2 that are separated by a staggered first row R1) is higher than the distance between two adjacent protrusions 2 in the same first row R1 or second row R2.

According to embodiments, considering a pattern of staggered first and second rows R1, R2, two first rows R1 and/or two second rows R2 (i.e. two first rows R1 that are separated by a staggered second row R2, and/or two second rows R2 that are separated by a staggered first row R1) are separated by a distance which is substantially equal to the length (first length L1; second length L2 in FIGS. 5 and 6 respectively) of a protrusion 2.

For example, the distance between two first rows R1 (that are not staggered) such as seen in FIG. 4, may range from 0.1 mm to 5 mm, from 0.2 mm to 3 mm, or from 0.25 mm to 2 mm in various embodiments.

The terms "first width W1", "first length L1" and "first distance D1" (in FIG. 5) and the terms "second width W2", "second length L2" and "second distance D2" (in FIG. 6) refer to the "final" features of the pattern of protrusions 2 provided on at least part of the first side 1a of the fabric 1 of the invention, i.e. to the "final" fabric.

Figure 7B:
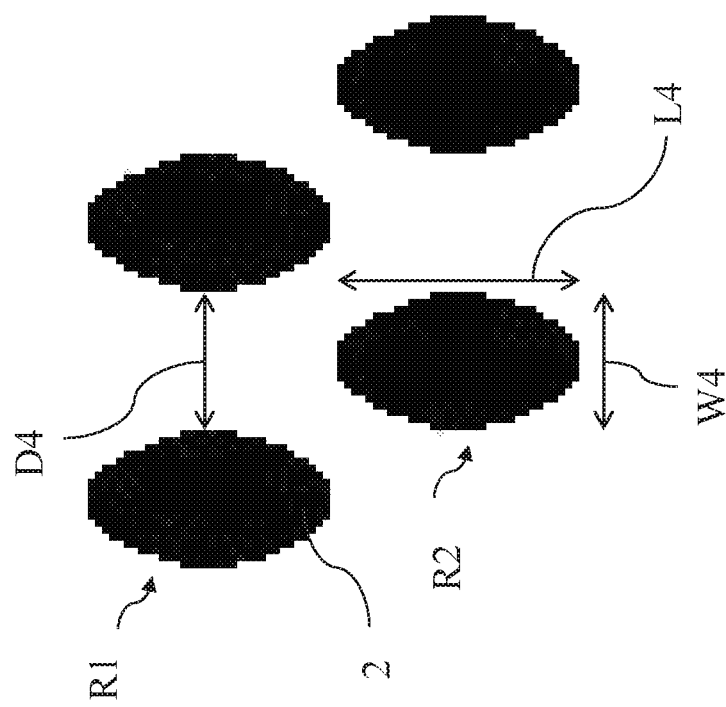
FIGS. 7A and 7B are a schematic representation of a pattern of substantially bi-dimensional elements comprising a heat-expanding material before the heat-treatment (FIG. 7A) and the pattern of protrusion deriving therefrom, after the heat-treatment (FIG. 7B).
Figure 7A:
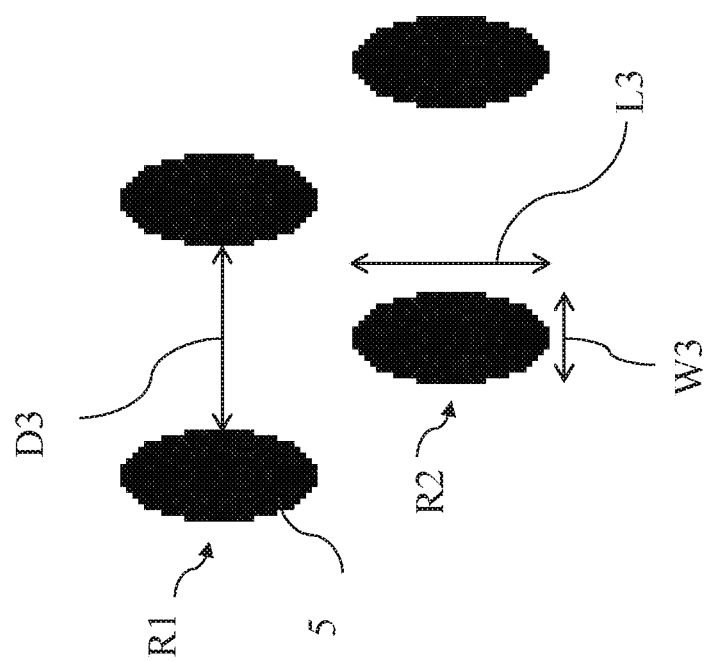

FIGS. 7A and 7B are, respectively, a schematic representation of a pattern of substantially bi-dimensional elements 5 comprising a heat-expanding material before the heat-treatment (FIG. 7A) and the pattern of protrusion 2 deriving therefrom, after the heat-treatment, wherein the protrusions 2 comprise the expanded heat-expanding material (FIG. 7B).

FIG. 7A shows an exemplary pattern of substantially bi-dimensional elements 5, comprising a heat-expanding material, that can be provided to a fabric 1, e.g. by printing.

In FIG. 7A the substantially bi-dimensional elements 5 are arranged in staggered rows R1, R2; schematically, a first row R1, and a second row R2, which is staggered with respect of the first row R1, are shown.

The substantially bi-dimensional elements 5 in the same first row R1 or second row R2 are spaced apart one to another by an initial distance D3.

The substantially bi-dimensional elements 5 have a predetermined initial width W3 and a predetermined initial length L3.

The fabric 1 provided with the substantially bi-dimensional elements 5 is heated; in this way, the heat-expanding material increases its volume, i.e. "expands", to provide a pattern of protrusions 2, which comprise the expanded heat-expanding material.

In other words, the heat-treatment causes the expansion of the heat-expanding material, so that a substantially bi-dimensional element 5 increases its volume to form a tridimensional structure, i.e. a protrusion 2.

The shape of the base 4 of the protrusions 2 substantially "corresponds" to the shape of the substantially bi-dimensional elements 5 comprising the heat-expanding material provided onto the fabric 1 before the expansion, i.e. before the heat-treatment. In the embodiment of FIGS. 7A and 7B, the substantially bi-dimensional elements 5 are provided on the fabric with an oval shape; therefore, the protrusions 2 deriving from such elements 5 have a substantially oval shape.

Of course, after the "expansion" (i.e., after the heat-treatment) the final width W4 and the final length L4 of a protrusion 2 (FIG. 7B) are generally greater than the initial width W3 and the initial length L3 of the substantially bi-dimensional element 5 (FIG. 7A) from which the protrusion 2 derives.

When a heat-expanding material (or a mixture comprising it) is applied before the heat-treatment, i.e. before the expansion, the heat-expanding material is applied onto the fabric according to a pattern of substantially bi-dimensional elements 5 that allows to obtain a pattern of protrusions 2 that are spaced apart by the selected final distance D4.

In other words, the initial width W3 and the initial length L3 of each substantially bi-dimensional element 5, as well as the initial distance D3 between such substantially bi-dimensional elements 5, are selected in order to obtain, after the heat-treatment a pattern of protrusions 2 having predetermined final width W4, final length L4 and final distance D4.

As above mentioned, the final width W4 and the final length L4 of a protrusion 2 are generally greater than the initial width W3 and the initial length L3 of the substantially bi-dimensional element 5 from which the protrusion 2 derives.

Conversely, the final distance D4 between two adjacent protrusions 2 is generally smaller than the initial distance D3 between two adjacent substantially bi-dimensional elements 5 from which the protrusion 2 derives. For example, a pattern of substantially bi-dimensional elements 5 may be provided to the fabric 1, such that two adjacent elements 5 in the same row R1, R2 are spaced apart one another by an initial distance D3 which is substantially two times the initial width W3 of the elements 5 before the heat-treatment while, after the heat-treatment, the pattern of protrusions 2 is deriving from the elements 5 is such that the final distance D4 between two adjacent protrusions 2 in the same row R1, R2 is substantially equal to the final width W4 of a protrusion 2.

The initial dimension of the substantially bi-dimensional elements 5 and the initial distance D3 between elements 5 may be selected in order to obtain a pattern of protrusions 2 wherein the protrusions 2 have a predetermined final width W4, final length L4, and wherein the protrusions 2 are spaced from one another by a preselected final distance D4.

Condition and parameters of the production process of the fabric 1 of the invention, such as, for example, the heating temperature and the duration of the heat-treatment, may be adjusted in order to obtain a pattern of protrusions 2 having predetermined features, e.g. predetermined final width W4 and predetermined final length L4 of the protrusions 2, and a predetermined final distance D4 between the protrusions 2.

The terms "initial width W3", "initial length L3" and "initial distance D3" (in FIG. 7A) refer to the "initial" features of the pattern of substantially bi-dimensional elements provided to the fabric 1, i.e. to the fabric before the heat-treatment, i.e. before the "conversion" of the substantially bi-dimensional elements 5 into protrusions 2.

Conversely, the terms "final width W4", "final length L4" and "final distance D4" which refer to the embodiment schematically represented in FIG. 7B, refer to the "final" features of the pattern of protrusions 2 provided on at least part of the first side 1a of the fabric 1 of the invention, i.e. to the "final" fabric, i.e. after the "conversion" of the substantially bi-dimensional elements 5 into protrusions 2.

As above discussed, the present invention has several advantages over known fabrics and garments for counteracting and reducing cellulite.

For example, the fabric of the invention provides beneficial effect to the wearer (e.g., reducing cellulite), and is comfortable to wear, even for prolonged time.

Additionally, in various embodiments, the polymeric layer protects the protrusions from wear-damage, thus prolonging the life of the fabric and of the garments comprising it.

Moreover, it has been observed that wearing of a garment which is made with the fabric of the invention, induces an increasing of the temperature at level of the skin of the wearer, i.e., between the skin of the wearer and the garment on the invention, further providing beneficial effects in alleviating and diminishing cellulite. For example, it has been observed that the mechanical friction of the fabric of the invention on the skin of a user, in addition to a massage effect to the skin of the user, also provides for an increase of the temperature of the skin of the user.

Mechanical friction between the fabric of the invention and the skin of a user may occur, For example, with every-day activity movements and/or with physical exercise.

Wearing tests were carried out: three pairs of pants, produced with the fabric of the invention, have been worn by three persons for three hours; the temperature at the level of the skin of the user was measured with a thermal camera before the wearing test and after three hours of wearing the pants produced with the fabric of the invention.

The obtained results are indicated in Table 1.

TABLE 1

|  | Before Wearing | After Wearing |
|---|---|---|
| Wearer 1 | 27.4° C. | 28.7° C. |
| Wearer 2 | 30.4° C. | 32.5° C. |
| Wearer 3 | 30.9° C. | 32.5° C. |

As can be observed, after three hours of wearing a garment produced with the fabric of the invention, the temperature at the level of the skin of the wearer increased up to about 7% (Wearer 2).

In addition to the massage effect, such an increase of the temperature at level of the skin of the wearer, provides for additional beneficial effects in alleviating, i.e. diminishing cellulite.

The invention claimed is:

1. A fabric (1) having a first side (1a) and a second side (1b), said fabric (1) comprising a plurality of protrusions (2) at least on part of said first side (1a) as a pattern of said protrusions (2), wherein said protrusions (2) comprise an expanded heat-expanding material, wherein said fabric (1) is an elastic woven fabric wherein the elasticity of said elastic woven fabric in warp direction, or in weft direction, or both in warp and weft direction is at least 15% (measured according to ASTM D3107—Stretch, after 3 home washes), and wherein said protrusions have a height ranging from 0.05 to 0.5 mm, and wherein at least said first side (1a) is substantially completely coated with a polymeric layer (3), whereby said protrusions are completely coated.

2. The fabric (1) according to claim 1, wherein said heat-expanding material comprises one of a polymeric heat-expanding material and a polymeric heat-expanding material including an expanding ink.

3. The fabric (1) according to claim 1, wherein said heat-expanding material comprises one of a first acrylic polymer based printing paste comprising an expanding ink and a silicone acrylic polymer based printing paste comprising an expanding ink.

4. The fabric (1) according to claim 1, wherein said polymeric layer (3) comprises a polyurethane.

5. The fabric (1) according to claim 1, wherein said polymeric layer (3) is a polymeric film.

6. The fabric (1) according to claim 1, wherein said polymeric layer (3) has a thickness ranging from 0.0015 mm to 0.03 mm.

7. The fabric (1) according to claim 1, wherein said protrusions (2) are arranged in parallel staggered rows (R1, R2).

8. The fabric (1) according to claim 1, wherein said protrusions (2) are spaced apart from one another by a distance substantially equal to a width of one of said protrusions (2).

9. The fabric (1) according to claim 1, wherein said protrusions (2) are positioned in staggered rows (R1, R2), such that a first said protrusion (2) in a first row (R1) is disposed substantially halfway between two adjacent ones of said protrusions (2) in rows (R2) adjacent said first row (R1).

10. The fabric (1) according to claim 1, wherein each said protrusion (2) is surrounded by six adjacent ones of said protrusions (2) positioned in a substantially hexagonal shape.

11. The fabric (1) according to claim 1, wherein said protrusions (2) have a base (4), said base (4) having a shape that is substantially an oval, an ellipse, a circle or a polygon.

12. The fabric (1) according to claim 1, wherein said fabric has a thickness and said protrusions (2) have a height that is less than said thickness.

13. The fabric (1) according to claim 1, wherein a distribution of the protrusions (2) ranges from 20 protrusions/cm2 to 5 protrusions/cm2.

14. The fabric (1) according to claim 1, wherein at least one of: said elasticity of said elastic woven fabric in warp direction lies within a range of 50% to 100% (measured according to ASTM D3107—Stretch, after 3 home washes); and, said elasticity of said elastic woven fabric (1) in weft direction lies within a range of 50% to 100% (measured according to ASTM D3107—Stretch, after 3 home washes).

15. The fabric (1) according to claim 1, wherein stiffness of said fabric (1) ranges from 2N to 0.75N measured according to ASTM D4032.

16. The fabric (1) according to claim 1, wherein the elasticity of said elastic woven fabric in warp direction, or in weft direction, or in both warp and weft direction lies within a range of 15% to 100% (measured according to ASTM D3107—Stretch, after 3 home washes).

17. A garment comprising a fabric (1) according to claim 1, wherein said first side (1*a*) contacts the body of a user when the garment is worn.

18. The garment according to claim 17, wherein different parts of said garment include different patterns of said protrusions (2).

* * * * *